United States Patent
Eder et al.

(10) Patent No.: US 9,989,132 B2
(45) Date of Patent: Jun. 5, 2018

(54) DRIVE DEVICE FOR MEDICAL OR DENTAL TOOL

(71) Applicant: W&H Dentalwerk Bürmoos GmbH, Bürmoos (AT)

(72) Inventors: Karlheinz Eder, Lamprechtshausen (AT); Michael Rothenwaender, Lamprechtshausen (AT); Josef Spitzauer, Oberndorf (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 1051 days.

(21) Appl. No.: 14/284,288

(22) Filed: May 21, 2014

(65) Prior Publication Data

US 2014/0318287 A1    Oct. 30, 2014

Related U.S. Application Data

(63) Continuation of application No. PCT/EP2012/073144, filed on Nov. 21, 2012.
(Continued)

(30) Foreign Application Priority Data

Nov. 21, 2011 (EP) .................................. 11189869
Mar. 16, 2012 (EP) .................................. 12159781

(51) Int. Cl.
    *A61C 1/18*    (2006.01)
    *F16H 19/08*   (2006.01)
    (Continued)

(52) U.S. Cl.
    CPC ............. *F16H 19/08* (2013.01); *A61C 1/00* (2013.01); *A61C 1/07* (2013.01); *A61C 1/185* (2013.01);
    (Continued)

(58) Field of Classification Search
    CPC .......... A61C 1/148; A61C 1/185; A61C 1/186
    (Continued)

(56) References Cited

U.S. PATENT DOCUMENTS 2,538,620 A    1/1951  Heinrich
3,678,745 A *  7/1972  Teng ................... F41J 13/00
                                                73/167
(Continued)

FOREIGN PATENT DOCUMENTS

EP     1078606       2/2001
JP     1-107312 U    7/1989
WO     WO2011/089348 7/2011

OTHER PUBLICATIONS

International Search Report for PCT/EP2012/073144 (dated Aug. 8, 2013).
(Continued)

*Primary Examiner* — Ralph Lewis
(74) *Attorney, Agent, or Firm* — Klarquist Sparkman, LLP

(57) ABSTRACT

Various mechanical drive devices, mechanical gears, combinations thereof and medical or dental treatment devices with such mechanical drive devices or gears are described. The mechanical drive devices and mechanical gears convert a unidirectional rotational movement received by a motor drive into a multidirectional movement, so that a tool-holding device of the treatment device can be induced to a multidirectional movement, in particular to a, preferably simultaneous, lifting and rotating movement or to a lifting and oscillating rotational movement with a reduced rotational speed.

20 Claims, 6 Drawing Sheets

Related U.S. Application Data

(60) Provisional application No. 61/562,375, filed on Nov. 21, 2011.

(51) Int. Cl.
    *A61C 1/00*         (2006.01)
    *F16H 35/02*      (2006.01)
    *A61C 1/07*         (2006.01)

(52) U.S. Cl.
    CPC ...... *F16H 35/02* (2013.01); *F04C 2270/0421* (2013.01); *Y10T 74/1856* (2015.01)

(58) Field of Classification Search
    USPC .......................................................... 433/118
    See application file for complete search history.

(56) References Cited

U.S. PATENT DOCUMENTS

| | | |
|---|---|---|
| 2,374,718 A | 5/1975 | Andrew |
| 4,718,851 A * | 1/1988 | Kuhn ................. A61C 1/185 433/122 |
| 4,834,652 A | 5/1989 | Luiset |
| 5,584,689 A | 12/1996 | Loge |
| 6,293,795 B1 | 9/2001 | Johnson |
| 9,743,998 B2 * | 8/2017 | Bierbaum ............. A61C 1/186 |

OTHER PUBLICATIONS

Office Action for Japanese Patent Application No. 2015-170944 (dated Jul. 26, 2016).

* cited by examiner

FIG. 3
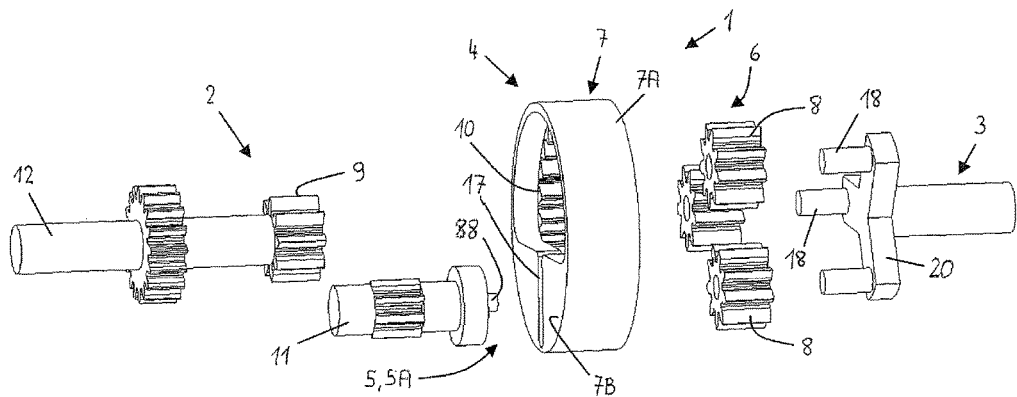
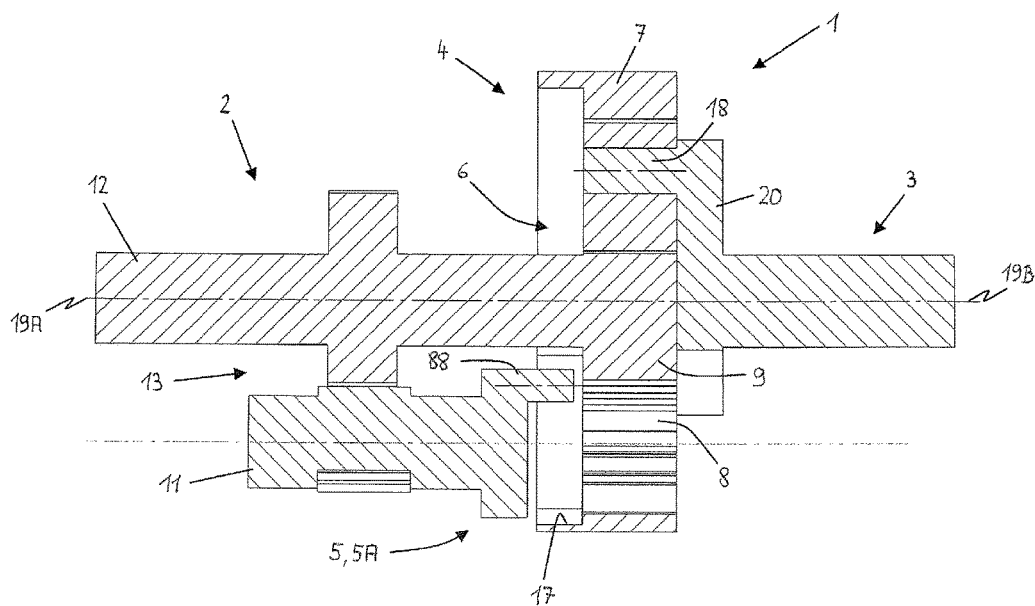
FIG. 4

FIG. 10
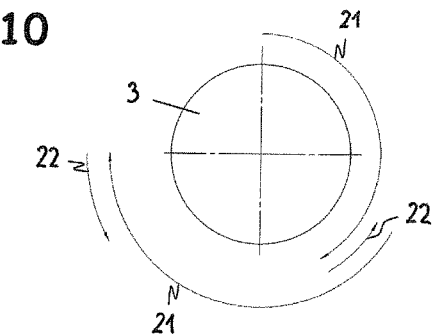
FIG. 11
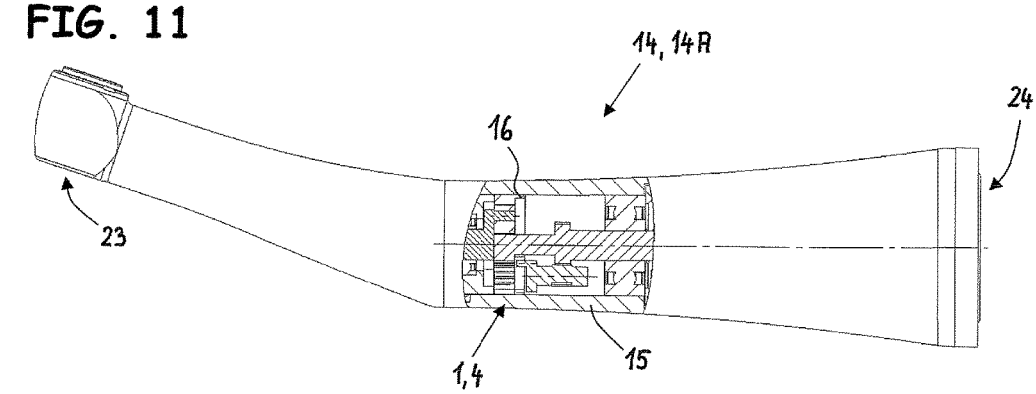
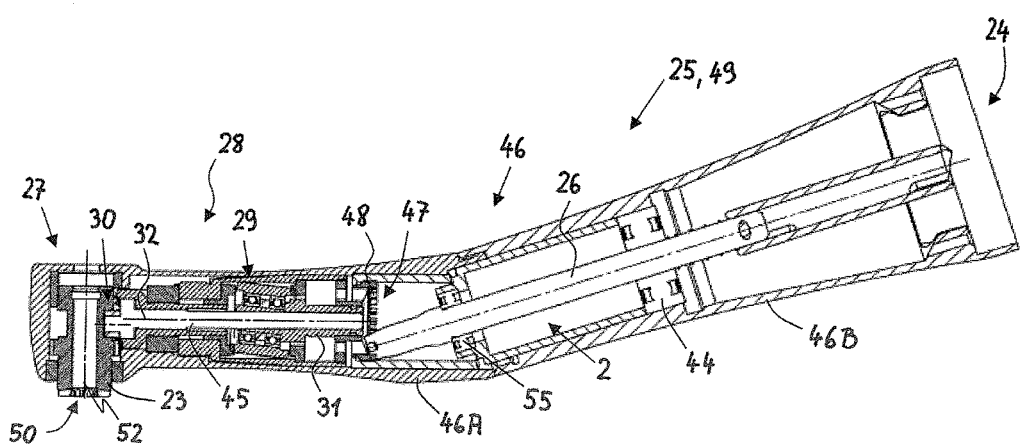
FIG. 12

DRIVE DEVICE FOR MEDICAL OR DENTAL TOOL

CROSS REFERENCE TO RELATED APPLICATIONS

This application is a U.S. bypass continuation application of international application PCT/EP2012/073144, filed on Nov. 21, 2012, which in turn claims priority from pending European Patent Applications No. EP11189869.8, filed Nov. 21, 2011, and EP12159781.9, filed Mar. 16, 2012. The benefit of prior U.S. Provisional Application No. 61/562,375, filed Nov. 21, 2011, is also claimed. The prior applications are incorporated herein by reference.

BACKGROUND

The present application relates to a drive device for a medical or dental tool, which is designed to convert a unidirectional rotational movement into a multidirectional rotational movement in order to operate the tool with this multidirectional movement.

A drive device, which converts a unidirectional rotational movement into a multidirectional movement in the form of a simultaneous or superimposed lifting and reduced-speed rotational movement, is known from the patent application WO 2011/089348 A1. This drive device, which is arranged in an angled handpiece, comprises a drive shaft, which can be connected to a motor and transmits a unidirectional rotational movement, a multistage planetary gear for reducing the rotational speed of the rotational movement, a shaft for transmitting the reduced-speed rotational movement and an eccentric shaft for generating the lifting movement.

This drive device has a number of disadvantages. To significantly reduce the rotational speed of the rotational movement, several planetary gears arranged in succession, for example, three planetary gears are provided, resulting in a need for a large amount of space. Because of this great need for space, the planetary gears can be arranged only in the rear section of the handpiece, which is at a distance from the head part of the angled handpiece and is separated by a bend or an angle (see FIG. 1 of WO 2011/089348 A1). However, then it is again necessary to provide two gears in the bend of the handpiece, a first gear for transmitting the reduced-speed rotational movement of the planetary gear and a second gear for transmitting the rotational movement to the eccentric shaft. Finally, the use of several planetary gears necessitates a variety of individual components and accordingly results in a high cost of manufacturing and assembly.

It would thus be desirable to create a drive device without the disadvantages mentioned above, such that it will convert a unidirectional rotational movement into a multidirectional movement in the form of a lifting and rotating movement, preferably simultaneously or superimposed, wherein the rotational speed of the rotational movement is preferably changed, in particular being reduced. In particular, the drive device should be as compact as possible, require little space, consist of a small number of individual parts, permit a great reduction in rotational speed and preferably be positionable between the angle and the head part of the angled handpiece.

Another drive device, which creates a multidirectional movement in the form of a multidirectional rotational movement, is known from U.S. Pat. No. 6,293,795 B1. This drive device comprises a handpiece, in particular an endodontic handpiece with a tool, for example, an endodontic file, which is driven by an electric motor. An electronic control unit including a microcontroller operates the electric motor in such a way that the file runs through a multidirectional rotational movement in the form of an oscillating rotational movement. The oscillating rotational movement comprises alternately a rotation of the tool about a first angle of rotation in a first direction of rotation and about a second angle of rotation in a second direction of rotation in the opposite direction, such that the first and second angle of rotations have different amounts. Due to the oscillating rotational movement tissue is removed, in particular tissue in the dental root canal, preferably by rotation of the tool in one direction of rotation, and this tissue is conveyed in the direction of the dental crown, preferably by rotation of the tool in the opposite direction of rotation.

One disadvantage of this drive device is that an electric control unit including a microcontroller is required for operation of the tool. There is thus a substantial additional technical and financial cost required for implementation of the oscillating rotational movement, in particular for users who have a treatment device that is operated only pneumatically.

Accordingly, it would be desirable to create an alternative drive device that would induce an oscillating rotational movement of a medical or dental tool and in particular could also be used with treatment equipment that is operated only pneumatically.

SUMMARY

According to one embodiment, a medical or dental treatment device is provided, comprising: a drive shaft, which is configured for transmission of a unidirectional rotational movement, a tool-holding device for holding a tool, which is arranged in a head part of the treatment device, such that it can be induced to a, preferably simultaneous, rotational and lifting motion, as well as a mechanical gear arrangement, which is designed to convert the unidirectional rotational movement into a, preferably simultaneous, lifting and rotational movement, so that the tool-holding device can be moved in a, preferably simultaneous, rotational and lifting motion, wherein the gear arrangement has a gear for changing, in particular reducing, the rotational speed of the unidirectional rotational movement and also has an eccentric gear. The gear for changing the rotational speed of the unidirectional rotational movement comprises: an input shaft with an axis of rotation, an output shaft connected to the tool-holding device, an extension connected to the input shaft having a central axis, wherein the central axis is arranged at an angle to the axis of rotation of the input shaft, a first row of teeth in a rotationally fixed arrangement with a plurality of teeth, a second row of teeth which is arranged rotatably and is connected to the output shaft and has a plurality of teeth, a sleeve arranged rotatably on the extension connected to the input shaft, having on its first end a third row of teeth and on its second end a fourth row of teeth, wherein the sleeve is arranged between the first row of teeth and the second row of teeth, such that at least one tooth of the third row of teeth meshes with at least one tooth of the first row of teeth and at least one tooth of the fourth row of teeth meshes with at least one tooth of the second row of teeth to induce a change in the rotational speed of the output shaft in relation to the input shaft.

A gear designed in this way for changing the rotational speed of the unidirectional rotational movement is very compact and needs only a small amount of space, so that it can be integrated more easily into a medical or dental treatment device, in particular into a handpiece or contra-angle handpiece. It consists of a comparatively small number of individual parts and permits in particular a wide range of rotational speed reductions, for example, beginning at 1:25 up to very high step-down ratios of 1:900, for example, or even more.

Especially advantageous embodiments of this treatment device include, individually or in combination, that:

- at least one bearing device is provided on the extension connected to the input shaft, so that the sleeve arranged on the extension is rotatable in relation to the extension, wherein in particular one end of the extension is designed as a free end, which extends freely and unsupported beyond the bearing device in the direction of the tool-holding device.
- the angle formed by the central axis of the extension connected to the input shaft and the axis of rotation of the input shaft amounts to approximately 5°-15°.
- the angle formed by the extension connected to the input shaft and the input shaft amounts to approximately 5°-15°.
- based on the central axis, the axial length of the extension connected to the input shaft is approximately 3-7 mm.
- the bearing device on the extension connected to the input shaft is designed as a roller bearing, in particular as a ball bearing or as a sliding bearing.
- the bearing device surrounds the extension connected to the input shaft.
- the bearing device is arranged between the extension connected to the input shaft and the sleeve arranged on the extension.
- the treatment device or the gear for changing the rotational speed of the unidirectional rotational movement comprises a disk-shaped or plate-shaped carrier with a first surface area and a second surface area arranged essentially parallel to the first surface area, wherein the first row of teeth, arranged in a rotationally fixed manner, is provided on the first surface area such, that its teeth point in the direction of the second row of teeth, and wherein the second surface area is preferably designed as a bearing seat for a bearing element supporting the input shaft, in particular for a roller bearing or a ball bearing.
- the first row of teeth, arranged in a rotationally fixed manner, is designed in one piece with the plate-shaped carrier.
- the plate-shaped carrier is attached to a rotationally fixed component of the treatment device, in particular to the outer sleeve of the treatment device, preferably by means of a shoulder or a setback on a corresponding shoulder or a corresponding protrusion on the treatment device.
- the bearing element is supported directly on the second surface area.
- the plate-shaped carrier has a borehole, preferably a central hole through which at least one of the following components extends: the input shaft of the gear for changing, in particular reducing, the rotational speed of the unidirectional rotational movement, a drive shaft for transmitting a unidirectional rotational movement, the shaft driving the eccentric gear, in particular a shaft connected to a part of the eccentric gear, for example, to an eccentric pin.
- the eccentric gear can be driven by a shaft, which passes through the gear for changing the rotational speed of the unidirectional rotational movement. Preferably the shaft driving the eccentric gear is connected to a part of the eccentric gear, for example, an eccentric pin or a receptacle for an eccentric pin. Preferably a hole for the shaft driving the eccentric gear is provided on at least one of the following components of the gear for changing the rotational speed of the unidirectional rotational movement: on the input shaft, on the first row of teeth, arranged in a rotationally fixed manner, on the plate-shaped carrier with the first row teeth, on the extension connected to the input shaft, on the second row of teeth which is arranged rotatably and is connected to the output shaft, on the output shaft connected to the tool-holding device.
- the gear for changing the rotational speed of the unidirectional rotational movement and the shaft driving the eccentric gear are arranged essentially concentrically.
- the angle formed by the central axis of the extension connected to the input shaft and the axis of rotation of the shaft driving the eccentric gear amounts to approximately 5°-15°.
- the angle formed by the extension connected to the input shaft and the shaft driving the eccentric gear amounts to approximately 5°-15°.
- the shaft driving the eccentric gear, which is preferably provided with a part of the eccentric gear, is rotatably mounted in the output shaft, preferably by a sliding bearing.
- the output shaft and/or the extension and/or the input shaft is/are designed as a hollow shaft in which the shaft driving the eccentric gear, which is preferably provided with a part of the eccentric gear, is accommodated.
- the input shaft and/or the extension is/are connected, for example, by pressing, in a rotationally fixed manner to the shaft driving the eccentric gear, which is preferably provided with a part of the eccentric gear. They can thus be induced to movement in an advantageous manner by means of a joint shaft and/or a joint gear.
- the input shaft with the extension and the shaft driving the eccentric gear, which is preferably provided with a part of the eccentric gear can be rotated in relation to one another and can be driven at different rotational speeds in particular.
- the input shaft, the shaft driving the eccentric gear, which is preferably provided with a part of the eccentric gear, and preferably the first row of teeth arranged in a rotationally fixed manner are arranged concentrically with one another. Alternatively or additionally, the shaft driving the eccentric gear, which is preferably provided with a part of the eccentric gear, the second row of teeth and the output shaft are all arranged concentrically with one another.
- the treatment device comprises a medical or dental, handle element, for example a straight handpiece or a contra-angle handpiece, which is designed in particular for endodontic treatment.
- the treatment device, in particular the contra-angle handpiece, comprises a handle part, which has a section near the head and a rear section arranged in an angled or bent relation to the section near the head, wherein the gear for changing the rotational speed of the unidirectional rotational movement is arranged at least partially in the section near the head.
- the gear arrangement comprises an additional mechanical gear, which is designed to convert a unidirectional rotational movement into an oscillating rotational movement, so that the tool-holding device can be induced to an oscillating rotational movement, wherein the oscillating rotational movement preferably comprises an alternating rotation of the tool about a first angle of rotation in a first direction of rotation and by a second angle of rotation in a second direction of rotation, which is essentially opposite the first direction of rotation, wherein the first and second angles of rotation are preferably of different amounts. The rotational movement of the, preferably simultaneous, lifting and rotational movement as mentioned above, to which the tool-holding device can be induced thus comprises in particular an oscillating rotational movement. The gear for converting the unidirectional rotational movement into an oscillating rotational movement may preferably also be formed for reducing a rotational speed.

the gear for converting the unidirectional rotational movement into an oscillating rotational movement is provided between the eccentric gear, which is preferably provided on the tool-holding device, and the gear for changing, in particular reducing, the rotational speed of the unidirectional rotational movement. Preferably, the gear for changing, in particular reducing, the rotational speed is provided in the rear section and the gear for converting the unidirectional rotational movement into an oscillating rotational movement is provided in the section of the treatment device, in particular of the contra-angle handpiece, which is near the head and is arranged at an angle or with a bend to the rear section.

the gear for converting the unidirectional rotational movement into an oscillating rotational movement comprises a first element for converting the unidirectional rotational movement transmitted by the drive shaft into an oscillating movement, in particular into an oscillating pendulum movement or swivel movement, and comprises a second element for transmitting the unidirectional rotational movement.

an output shaft, which connects the tool-holding device to the gear for converting the unidirectional rotational movement into an oscillating rotational movement, is connected to the first element and/or the second element in such a way, that the oscillating movement, in particular the oscillating pendulum movement or pivoting movement, and the unidirectional rotational movement can be transmitted to the output shaft simultaneously.

the eccentric gear can be driven by a shaft, which is preferably provided with a part of the eccentric gear, which extends through the gear for converting the unidirectional rotational movement into an oscillating rotational movement and/or through the output shaft. Preferably, the gear for converting the unidirectional rotational movement into an oscillating rotational movement, in particular a central gearwheel of said gear, comprises a borehole to receive the shaft driving the eccentric gear.

the output shaft, which connects the tool-holding device to the gear for converting the unidirectional rotational movement into an oscillating rotational movement, is designed as a hollow shaft in which the shaft driving the eccentric gear, and which is preferably provided with a part of the eccentric gear, is accommodated. The output shaft and the shaft driving the eccentric gear can be operated in particular at different rotational speeds.

the first element for converting the unidirectional rotational movement transmitted by the drive shaft into an oscillating movement, in particular into an oscillating pendulum movement or pivoting movement comprises an (additional) eccentric gear, and the second element for transmitting the unidirectional rotational movement comprises a plurality of gearwheels.

According to another embodiment, a medical or dental treatment device is provided, comprising: a tool-holding device for holding a medical or dental tool and a drive device for the tool, which is designed to cause the tool to move with an oscillating rotational movement, wherein the oscillating rotational movement comprises an alternating rotation of the tool about a first angle of rotation in a first direction of rotation and in a second direction of rotation, which is essentially opposite the first direction of rotation, about a second angle of rotation, wherein the first and the second angles of rotation are preferably of different amounts, wherein the drive device has a drive shaft arrangement, which is designed for transmitting a unidirectional rotational movement, an output shaft, a mechanical gear that can be driven by the drive shaft arrangement and is designed to convert the unidirectional rotational movement transmitted by the drive shaft arrangement into an oscillating rotational movement and to transmit it to the output shaft, and an eccentric gear, which cooperates with the tool-holding device, so that the tool-holding device can advantageously be induced to a, preferably simultaneous, lifting and oscillating rotational movement.

Especially advantageous embodiments of this treatment device include, individually or in combination, that:

the eccentric gear cooperating with the tool-holding device can be driven by a shaft, which is preferably provided with a part of the eccentric gear, passing through the mechanical gear for converting the unidirectional rotational movement into an oscillating rotational movement, in particular passing through the central gearwheel of the mechanical gear. Preferably, the gear for converting the unidirectional rotational movement into an oscillating rotational movement, in particular a central gearwheel of said gear, comprises a hole to receive the shaft driving the eccentric gear.

the output shaft, which connects the tool-holding device to the gear for converting the unidirectional rotational movement to an oscillating rotational movement, is designed as a hollow shaft or has a borehole in which the shaft driving the eccentric gear, preferably provided with a part of the eccentric gear, is accommodated. The output shaft and the shaft driving the eccentric gear are movable in relation to one another in particular and/or can be operated at different rotational speeds.

the drive shaft of the mechanical gear for converting the unidirectional rotational movement into an oscillating rotational movement is designed as a hollow shaft or has a borehole, in which the shaft driving the eccentric gear, which is preferably provided with part of the eccentric gear, is accommodated.

the drive shaft of the mechanical gear for converting the unidirectional rotational movement into an oscillating rotational movement is connected in a rotationally fixed manner, for example, by pressing, to the shaft driving the eccentric gear, which is preferably provided with a part of the eccentric gear. The two shafts can therefore be induced to movement by a common drive shaft and/or a common gear in an advantageous manner the drive shaft of the mechanical gear for converting the unidirectional rotational movement into an oscillating rotational movement and the shaft driving the eccentric gear, which is preferably provided with a part of the eccentric gear, can be rotated relative to one another and can be operated at different rotational speeds in particular.

the treatment device additionally comprises a gear for transmitting and/or changing, in particular reducing, the rotational speed of the unidirectional rotational movement.

at least a part of the gear for transmitting and/or changing, in particular reducing, the rotational speed, in particular a gearwheel of the gear, is arranged directly on a shaft driving the eccentric gear, this shaft preferably being provided with a part of the eccentric gear, and/or is arranged on a drive shaft arrangement, which drives the mechanical gear for conversion of the unidirectional rotational movement into an oscillating rotational movement, so that the shaft driving the eccentric gear and the drive shaft arrangement driving the mechanical gear for conversion of the unidirectional rotational movement into an oscillating rotational movement can be driven jointly by the at least one part of the gear for transmitting and/or changing the rotational speed.

the gear for transmitting and/or changing, in particular reducing, the rotational speed comprises: an input shaft with an axis of rotation, an output shaft connected to the tool-holding device, an extension, which is connected to the input shaft and has a central axis, wherein the central axis is arranged at an angle to the axis of rotation of the input shaft, a first row of teeth, which is arranged in a rotationally fixed manner and has a plurality of teeth, a rotatably arranged second row of teeth having a plurality of teeth and connected to the output shaft, a sleeve rotatably arranged on the extension connected to the input shaft, this sleeve having a third row of teeth on its first end and having a fourth row of teeth on its second end, wherein the sleeve is arranged between the first row of teeth and the second row of teeth such, that at least one tooth of the third row of teeth meshes with at least one tooth of the first row of teeth and at least one tooth of the fourth row of teeth meshes with at least one tooth of the second row of teeth to achieve a change in the rotational speed of the output shaft relative to the input shaft.

at least one bearing device is provided on the extension connected to the input shaft, so that the sleeve arranged on the extension is rotatable in relation to the extension, wherein one end of the extension is designed as a free end, which extends freely and without support beyond the bearing device in the direction of the tool-holding device.

the angle formed by the extension connected to the input shaft and the input shaft amounts to approximately 5°-15°.

the axial length of the extension connected to the input shaft amounts to approximately 3-7 mm based on the central axis.

the bearing device on the extension connected to the input shaft is designed as a roller bearing, in particular as a ball bearing or as a sliding bearing.

the bearing device surrounds radially the extension connected to the input shaft.

the bearing device is arranged between the extension connected to the input shaft and the sleeve arranged on the extension.

the treatment device or the gear for changing the rotational speed of the unidirectional rotational movement comprises a disk-shaped or plate-shaped carrier having a first surface area and a second surface area, which is arranged to be essentially parallel to the first surface area, wherein the first row of teeth, which is arranged in a rotationally fixed manner, is provided on the first surface area such, that its teeth point in the direction of the second row of teeth, and wherein the second surface area is preferably designed as a bearing seat for a bearing element supporting the input shaft.

the first row of teeth, which is arranged in a rotationally fixed manner, is designed in one piece with the plate-shaped carrier.

the plate-shaped carrier is attached to a rotationally fixed component of the treatment device, in particular to the outer sleeve of the treatment device, preferably by means of a shoulder or a setback on a corresponding shoulder or a corresponding protrusion on the treatment device.

the bearing element is supported directly on the second surface area.

the plate-shaped carrier has a borehole, preferably positioned centrally, through which at least one of the following components extends: the input shaft of the gear for changing, in particular reducing, the rotational speed of the unidirectional rotational movement, a drive shaft for transmitting a unidirectional rotational movement, the shaft driving the eccentric gear, in particular a shaft, which is connected to a part of the eccentric gear, for example, an eccentric pin.

the gear for converting the unidirectional rotational movement into an oscillating rotational movement is provided between the eccentric gear, which is preferably provided on the tool-holding device, and the gear for transmitting and/or changing, in particular reducing, the speed of the unidirectional rotational movement.

the treatment device comprises a medical or dental handle element, for example, a straight handpiece or a contra-angle handpiece, which is designed in particular for endodontic treatments.

the treatment device, in particular the contra-angle handpiece, has a head part with the tool-holding device and a handle part, wherein the handle part has a section near the head part and a rear section arranged at an angle or curve in relation to the section near the head part, wherein the mechanical gear for converting the unidirectional rotational movement into an oscillating rotational movement is arranged at least partially in the section near the head part. Preferably, the gear for transmitting and/or changing, in particular reducing, the rotational speed of the unidirectional rotational movement is arranged at least partially in the rear section.

the drive shaft arrangement comprises a first drive shaft, on which at least a portion of the gear for transmission and/or for changing, in particular reducing, the rotational speed of the unidirectional rotational movement is provided, and a second drive shaft on which the gear for converting the unidirectional rotational movement into an oscillating rotational movement is provided, wherein the two drive shafts are interconnected by a gear. Preferably the gear connecting the two drive shafts is designed as a reduction gear or as a 1:1 gear. The first drive shaft is preferably provided essentially in the rear section and the second drive shaft is provided essentially in the section near the head part.

the two drive shafts are arranged at an angle to one another and/or the shaft driving the eccentric gear, which is preferably provided with a part of the eccentric gear, is arranged at an angle to the first drive shaft.

the mechanical gear for converting the unidirectional rotational movement into an oscillating rotational movement comprises a first element for converting the unidirectional rotational movement transmitted by the drive shaft arrangement into an oscillating movement, in particular an oscillating pendulum movement or pivoting movement, and a second element for transmitting the unidirectional rotational movement.

the output shaft is connected to the first element and/or to the second element such, that the oscillating movement, in particular the oscillating pendulum movement or pivoting movement and the unidirectional rotational movement can be transmitted simultaneously to the output shaft.

According to another embodiment, i.e., a third embodiment, a drive device for a medical or dental tool is provided, this drive device being designed to induce an oscillating rotational movement of the tool, wherein the oscillating rotational movement comprises an alternating rotation of the tool about a first angle of rotation in a first direction of rotation and in a second direction of rotation, which is substantially opposite the first direction of rotation, about a second angle of rotation, wherein the first and second angles of rotation are preferably of different amounts and wherein the drive device comprises: a drive shaft arrangement, which is designed for transmitting a unidirectional rotational movement, an output shaft and a mechanical gear that can be driven by the drive shaft arrangement and is designed to convert the unidirectional rotational movement transmitted by the drive shaft arrangement into an oscillating rotational movement and to transmit it to the output shaft.

By providing a mechanical gear, which converts a unidirectional rotational movement into an oscillating rotational movement, the drive device is independent of an electric power supply, in particular independent of an electric motor drive and/or an electric control and may thus be used advantageously with any treatment devices, in particular also with pneumatic treatment devices.

Particularly advantageous embodiments of this drive device comprise individually or in combination that:

the mechanical gear has a first element for converting the unidirectional rotational movement transmitted by the drive shaft arrangement into an oscillating movement, in particular into an oscillating pendulum movement or pivoting movement, and a second element for transmitting the unidirectional rotational movement.

the output shaft is connected to the first element and/or to the second element such that the oscillating movement, in particular the oscillating pendulum movement or pivoting movement, and the unidirectional rotational movement can be transmitted to the output shaft at the same time.

the first element for converting the unidirectional rotational movement transmitted by the drive shaft arrangement into an oscillating movement, in particular into an oscillating pendulum movement or pivoting movement, comprises an eccentric gear.

at least a part of the eccentric gear is provided on an internal gear or internally geared wheel of the mechanical gear, wherein the internal gear is preferably designed to be rotatable in relation to the drive shaft arrangement.

the second element comprises a plurality of gearwheels for transmitting the unidirectional rotational movement.

at least one of the gearwheels is mounted, preferably rotatable, on the output shaft, wherein in particular the oscillating movement generated by the first element can be transmitted to the output shaft through this at least one gearwheel connected to the output shaft.

at least one of the gearwheels of the second element for transmitting the unidirectional rotational movement is arranged in the internal gear.

the internal gear has internal gear teeth which mesh with the at least one gearwheel arranged in the internal gear.

at least one second, preferably peripheral, gearwheel, which is rotatably connected to the drive shaft arrangement or to the output shaft, rotates about a first, preferably central, gearwheel, which is connected in a rotationally fixed manner to the drive shaft arrangement or to the output shaft, wherein the at least one second gearwheel meshes with the internal gear teeth of the internal gear.

the drive shaft arrangement comprises a first drive shaft and a second drive shaft, wherein the first drive shaft is connected to the first element of the mechanical gear for conversion of the unidirectional rotational movement transmitted by the drive shaft arrangement into an oscillating movement, in particular into an oscillating pendulum movement or pivoting movement, and the second drive shaft is connected to the second element of the mechanical gear for transmitting the unidirectional rotational movement.

the first drive shaft and the second drive shaft are connected to one another by means of a distributor gear, so that they can be driven by the same motor.

a torque-limiting device is provided, preferably on the mechanical gear, for example, a friction clutch for limiting the torque that can be transmitted to the tool.

the output shaft is connected directly and/or fixedly to the second element for transmitting the unidirectional rotational movement, in particular to at least one of the gearwheels of the second element.

the output shaft is connected directly and/or fixedly to the first element for converting the unidirectional rotational movement transmitted by the drive shaft arrangement into an oscillating movement, in particular into an oscillating pendulum movement or pivoting movement, in particular being connected to the eccentric gear, preferably to the internal gear, and wherein a part of the first element, in particular of the eccentric gear, for example, the eccentric or the receptacle, is provided on a carrier of the at least one peripheral gearwheel, for example, on the connecting element.

According to an embodiment, a medical or dental treatment device, such as a medical or dental handle element is provided, these being designed in particular for endodontic treatments and having a drive device as described above according to the third embodiment, in particular a drive device having a mechanical gear that can be driven by the drive shaft arrangement and is designed to convert the unidirectional rotational movement transmitted by the drive shaft arrangement into an oscillating rotational movement and to transmit it to the output shaft. The treatment device or the handle element preferably comprises a sleeve with a bearing surrounding the mechanical gear, in particular a sliding bearing or needle bearing by means of which the mechanical gear, preferably the eccentric gear of the mechanical gear, in particular the internal gear of the eccentric gear of the mechanical gear, is rotatably supported in the treatment device or the handle element.

According to another embodiment, a medical or dental treatment device medical or dental handle element is provided, which is designed in particular for endodontic treatments and which comprises: a drive shaft, which is designed for transmitting a unidirectional rotational movement, a tool-holding device for holding a tool and a gear arrangement that connects the drive shaft to the tool-holding device and comprises a plurality of mechanical gears, preferably three, and being designed to convert the unidirectional rotational movement transmitted by the drive shaft such that the tool-holding device can be induced to execute a, preferably simultaneous, lifting and oscillating rotational movement with a reduced rotational speed in comparison with the rotational speed of the unidirectional rotational movement transmitted by the drive shaft. The oscillating rotational movement preferably comprises an alternating rotation of the tool about a first angle of rotation in a first direction of rotation and in a second direction of rotation, which essentially is opposite the first direction of rotation, about a second angle of rotation, wherein the first and second angles of rotation are preferably of different amounts. The gear arrangement preferably includes a gear for reduction of the rotational speed of the unidirectional rotational movement, an eccentric gear and a gear, which is designed to convert the unidirectional rotational movement transmitted by the drive shaft into an oscillating rotational movement. These three aforementioned gears preferably have one or more of the specific embodiments mentioned above.

A preferred embodiment of a use of a medical or dental treatment device or handle element as described above comprises an endodontic treatment.

BRIEF DESCRIPTION OF DRAWINGS

Preferred embodiments are explained in greater detail below with reference to the accompanying drawings:

FIGS. 1-4 show a first embodiment of a drive device having a mechanical gear, which converts a unidirectional rotational movement into an oscillating rotational movement.

FIG. 10 shows an embodiment of an oscillating rotational movement which can be created by a drive device having a mechanical gear which converts a unidirectional rotational movement into an oscillating rotational movement.

FIG. 11 shows a medical or dental treatment device having a handle element in which a drive device with a mechanical gear that converts a unidirectional rotational movement into an oscillating rotational movement is provided.

FIG. 12 shows a medical or dental treatment device comprising a gear arrangement, which has a gear for changing, in particular reducing, the rotational speed and an eccentric gear, so that the tool-holding device of the treatment device can be induced to a, preferably simultaneous, lifting and rotational movement with an altered rotational speed.

DETAILED DESCRIPTION

Figure 1:
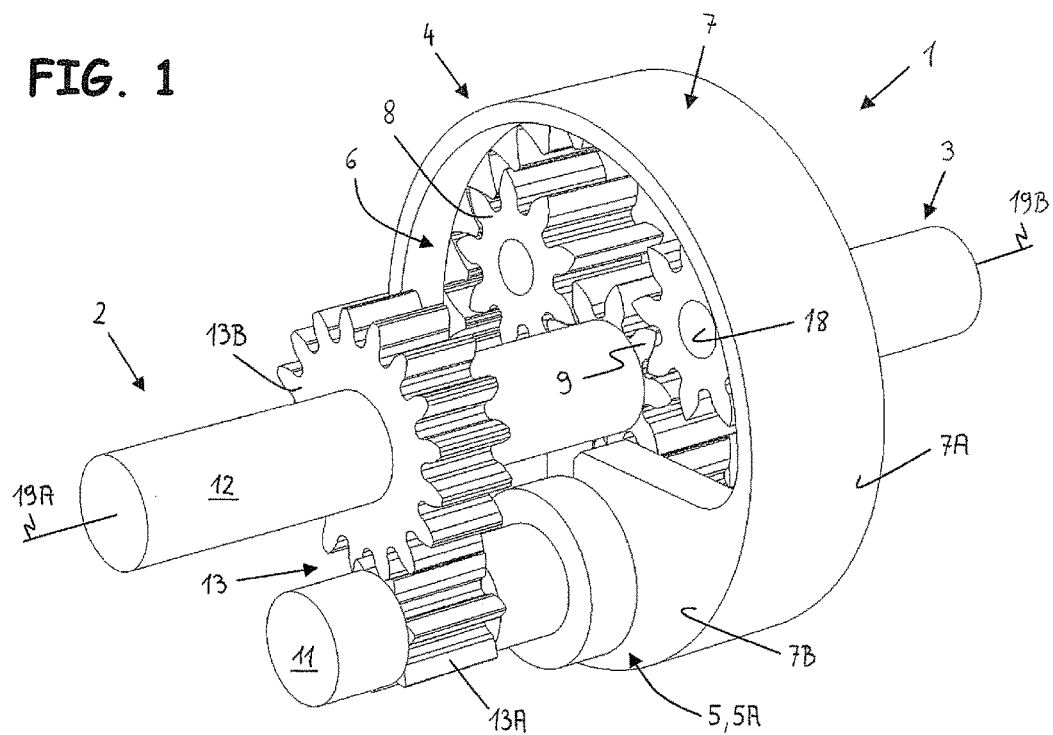
Figure 2:
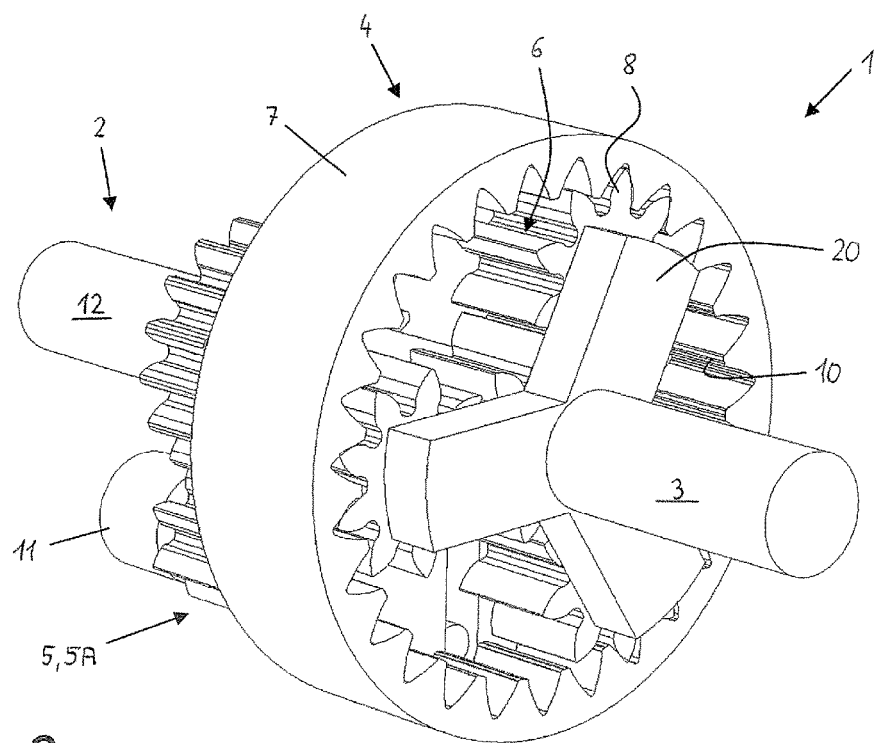

FIGS. 1-4 and 5-7 show different embodiments of drive devices 1, 1A for a medical or dental (including surgical), preferably endodontic, tool. The common components and/or functions of these two drive devices 1, 1A are described below:

The drive devices 1, 1A each have a mechanical gear 4 which is designed to convert a unidirectional rotational movement into an oscillating rotational movement. An oscillating rotational movement refers to a rotational movement that comprises an alternating rotation of the tool in a first direction of rotation about a first angle of rotation and in a second direction of rotation, which is essentially opposite the first direction of rotation about a second angle of rotation, wherein the first and second angles of rotation are preferably of different amounts. In other words an oscillating rotational movement comprises a movement sequence in which, for example, a shaft element or tool connected to the mechanical gear 4 rotates alternately clockwise or counter-clockwise with a first angle of rotation and then clockwise or counterclockwise with a second angle of rotation, wherein the angles of rotation are preferably of different amounts. On the whole this movement sequence yields a rotational movement of the shaft element or tool in a preferential direction or working direction because of the different sizes of the angles of rotation, wherein the shaft element or tool executes an oscillating movement because of the different directions of rotation. Thus the oscillating rotational movement permits alternating removal of tissue in a preparation area, in particular from the dental root canal, and conveyance of the removed tissue away from the preparation area, for example, in the direction of the dental crown or the mechanical gear 4.

The drive devices 1, 1A have, in addition to the gear 4, a drive shaft arrangement 2 and an output shaft 3, both of which are operatively connected to the gear 4, in particular being mechanically connected. The drive shaft arrangement 2 is or can be connected to a motor drive, for example, to a pneumatically operable motor or an electrically operable motor. The motor drive generates a unidirectional rotational movement clockwise or counterclockwise which is transmitted by the drive shaft arrangement 2 to the gear 4 or is made available to the gear 4. FIGS. 1-7 show that the drive shaft arrangement 2 preferably has at least two drive shafts 11, 12, the function of which will be discussed further below.

The output shaft 3 transmits the oscillating rotational movement generated by the gear 4 to the tool and/or to a tool-holding device.

The mechanical gear 4 comprises a first element 5 for converting the unidirectional rotational movement transmitted by the drive shaft arrangement 2 into an oscillating movement, in particular into an oscillating pendulum movement or pivoting movement, and a second element 6 for transmitting the unidirectional rotational movement. In particular the output shaft 3 is connected to the first element 5 and/or the second element 6 such that the oscillating movement and the unidirectional rotational movement can be transmitted at the same time to the output shaft 3.

The first element 5 for converting the unidirectional rotational movement transmitted by the drive shaft arrangement 2 into an oscillating movement, in particular an oscillating pendulum movement or pivoting movement, preferably comprises an eccentric gear 5A. The eccentric gear 5A comprises an eccentric element 88, for example, an eccentric pin or an eccentric disk as well as a receptacle 17 for the eccentric element 88. The receptacle 17 may be designed, for example, as a groove, slot, channel, undercut or guide for the eccentric element 88. The eccentric element 88 is in particular arranged eccentrically in relation to an axis of rotation of the drive shaft arrangement 2, in particular to the axis of rotation of the first drive shaft 11. The eccentric element 88, in particular a pin-shaped eccentric element 88 may preferably be provided with a bearing, for example, a roller bearing, a needle bearing or a sliding bearing.

A first part of the eccentric gear 5A is provided on the drive shaft arrangement 2, in particular on its first drive shaft 11, preferably the eccentric element 88 (see FIG. 3, for example) but it is precisely possible in this way to arrange the receptacle 17 for the eccentric element 88 on the drive shaft arrangement 2. An additional part of the eccentric gear 5A, for example, the receptacle 17 or the eccentric element 88 is provided on the gear 4 itself, in particular on an internal gear 7 of the mechanical gear 4 (see FIG. 3 again). A wall section 7B extending from a jacket 7A of the internal gear 7 or a carrier for an eccentric part is preferably provided on the internal gear 7 such that the additional part of the eccentric gear 5A is arranged on this carrier or wall section. The wall section 7B or the carrier in particular extends radially from an edge or an end face of the jacket 7A, in particular into the inside clearance of the internal gear 7 bordered by the jacket 7A. The drive shaft 11 is arranged adjacent to the wall section 7B or to the carrier.

The internal gear 7 is designed to be rotatable, for example, pivotable in relation to the drive shaft arrangement 2, in particular to the first drive shaft 11. The internal gear 7 preferably has internal gear teeth 10 on its inside, in particular on the inside of the jacket 7A; the function of these teeth will be discussed in greater detail below.

The second element 6 for transmitting the unidirectional rotational movement preferably comprises a plurality of gearwheels 8, 8A, 9, 9A. In particular at least a portion of the second element 6 for transmitting the unidirectional rotational movement or at least one gearwheel 8, 8A, 9, 9A is surrounded by the internal gear 7 or is arranged in the internal gear 7. The gearwheels 8, 8A, 9, 9A are connected to the drive shaft arrangement 2, in particular to their second drive shaft 12, so that the drive shaft arrangement 2 transmits the unidirectional rotational movement to the gearwheels 8, 8A, 9, 9A and makes them rotate. Preferably at least one of the gearwheels 8, 8A, 9, 9A is connected to the drive shaft arrangement 2 in a rotationally fixed manner, in particular to its second drive shaft 12 for transmitting the unidirectional rotational movement.

In addition, it can be seen from FIGS. 1-7 that at least one, preferably several of the gearwheels 8, 8A, 9, 9A mesh with the internal gear teeth 10 of the internal gear 7, so that rotational movements and torques can be transmitted between the internal gear 7 and at least some of the gearwheels 8, 8A, 9, 9A.

The gearwheels 8, 8A, 9, 9A preferably comprise a central gearwheel 9, 9A which is surrounded by one or more, for example, two or three peripheral gearwheels 8, 8A. The central gearwheel 9, 9A is engaged with the at least one peripheral gearwheel 8, 8A so that rotational movements and torques can be transmitted between the central gearwheel 9, 9A and the at least one peripheral gearwheel 8, 8A. The at least one peripheral gearwheel 8, 8A preferably meshes with the internal gear teeth 10 of the internal gear 7. The at least one peripheral gearwheel 8, 8A is preferably arranged rotatably on shaft sections 18.

As already described above, the drive shaft arrangement 2 comprises a first drive shaft 11 and a second drive shaft 12, wherein the first drive shaft 11 is connected to the first element 5 of the mechanical gear 4 for converting the unidirectional rotational movement transmitted by the drive shaft arrangement 2 into an oscillating movement, in particular an oscillating pendulum movement or pivoting movement, and the second drive shaft 12 is connected to the second element 6 of the mechanical gear 4 for transmitting the unidirectional rotational movement. In order for the two drive shafts 11, 12 to be drivable by a common motor, a distributor gear 13 which connects the two drive shafts 11, 12 to one another is provided. The distributor gear 13 is formed, for example, by two intermeshing gearwheels 13A, 13B, wherein one gearwheel 13A, 13B each is mounted on a drive shaft 11, 12. The two gearwheels 13A, 13B may preferably have a different number of teeth to form a step-down or step-up gear, so that the two drive shafts 11, 12 rotate at different rotational speeds and/or torques. Preferably, the first drive shaft 11 connected to the first element 5 of the mechanical gear 4 for converting the unidirectional rotational movement transmitted by the drive shaft arrangement 2 into an oscillating movement is connected to the common motor by means of the distributor gear 13. The second drive shaft 12, which is connected to the second element 6 of the mechanical gear 4 for transmitting the unidirectional rotational movement, preferably transmits the rotational movement of the common motor to the first drive shaft 11 by means of the distributor gear 13.

An axis of rotation 19A of the drive shaft arrangement 2, in particular an axis of rotation 19A of one of the drive shafts 11, 12, and/or an axis of rotation 19B of the output shaft 3, preferably forms a central axis and/or an axis of rotation for at least parts of the mechanical gear 4, in particular for one of the gearwheels 8, 8A, 9, 9A, in particular the central gearwheel 9, 9A, and/or for the internal gear 7.

According to an embodiment it is also possible to provide several first drive shafts 11, wherein each of the first drive shafts 11 is connected to the first element 5 of the mechanical gear 4 for converting the unidirectional rotational movement transmitted by the drive shaft arrangement 2 into an oscillating movement, in particular into an oscillating pendulum movement or pivoting movement.

With reference to FIGS. 1-4, the functioning of the drive device 1 is described below.

After activation of a motor drive that is or can be connected to the drive shaft arrangement 2, the motor drive generates a unidirectional rotational movement, which is transmitted to the drive shaft arrangement 2, in particular to one of the two drive shafts 11, 12 and by means of the distributor gear 13 to the other one of the two drive shafts 11, 12, so that both drive shafts 11, 12 execute a unidirectional rotational movement, in particular in opposite directions.

The central gearwheel 9 which is connected to the second drive shaft 12 in a rotationally fixed manner is thus also set in rotation and drives the peripheral gearwheels 8 (namely three of them in FIGS. 1-4) because of the meshing engagement. The rotational direction of the peripheral gearwheels 8 which are set in rotation by the central gearwheel 9 is opposite the direction of rotation of the central gearwheel 9 and the second drive shaft 12. The peripheral gearwheels 8 which are arranged rotatably on the shaft sections 18 move along the inside wall of the internal gear 7 because of their meshing engagement with the internal gear teeth 10 of the internal gear 7. The peripheral gearwheels thus run through a rotational movement within the internal gear 7 or along its inside wall. The rotational movement of the peripheral gearwheels 8 is transmitted to the output shaft 3 by means of a connection of each peripheral gearwheel 8 or each shaft section 18 via a connecting element 20, for example, an arm or a web, to the output shaft 3. The gearwheels 8, 9 are thus part of the second element 6 for transmitting the unidirectional rotational movement from the drive shaft arrangement 2 to the output shaft 3. The directions of rotation of the drive shaft arrangement 2 and the output shaft 3 here are in the same directions. Through a corresponding choice of the gear teeth of the gearwheels 8, 9 it is additionally preferably possible for the second element 6 of the gear 4 to be designed as a step-down or step-up gear or as a 1:1 gear without a step-up or step-down gear ratio.

The first drive shaft 11 which also rotates unidirectionally drives the first element 5, i.e., the eccentric gear 5A of the gear 4 simultaneously, i.e., while the unidirectional rotational movement is being transmitted to the output shaft 3 by the second element 6. Because of the engagement of the eccentric element 88 in the receptacle 17 of the internal gear 7 and because of the rotational movement of the drive shaft 11 and thus of the eccentric element 88, the internal gear 7 is induced to an oscillating movement, in particular an oscillating pendulum movement or pivoting movement, about the axis of rotation 19A, 19B. The internal gear 7 which is designed to be rotatable with respect to the drive shaft arrangement 2 or the shafts 3, 11, 12, thus rotates or oscillates clockwise and counterclockwise in alternation about an angle of rotation.

Since the transmission of the unidirectional rotational movement by the second element 6 of the mechanical gear 4 and the oscillating movement of the internal gear 7, in which the peripheral gearwheels 9 move in relation to the internal gear 7, induced by the first element 5 of the gear 4 take place simultaneously, as already discussed above, the unidirectional rotational movement is superimposed by the oscillating movement. In particular at least one of the gearwheels 8, 8A, 9, 9A is rotatably connected to the output shaft 3, wherein the oscillating movement generated by the first element 5, in particular the internal gear 7, can be transmitted to the output shaft 3 by means of said at least one gearwheel 8, 8A, 9, 9A, which is connected rotatably to the output shaft 3. Especially preferably at least one of the gearwheels 8, 8A, 9, 9A is mounted, in particular rotatably, on the output shaft 3, wherein preferably the oscillating movement generated by the first element 5 can be transmitted to the output shaft 3 by means of this at least one gearwheel 8, 8A, 9, 9A that is connected to the output shaft 3.

A movement of the internal gear 7 in the same direction as the rotational movement of the peripheral gearwheels 8 preferably induces a rotation of the output shaft 3 or of a tool that is or can be connected to the output shaft 3 in the first direction, in particular in a preferential direction or working direction, already mentioned above, and/or induces a movement about a first large angle of rotation of the output shaft 3 or of the tool. Accordingly a movement of the internal gear 7 opposite the rotational movement of the peripheral gearwheels 8 induces a rotation of the output shaft 3 or of a tool that is or can be connected to the output shaft 3 in a second opposite direction, in particular a direction that is opposite the preferential direction or working direction or in a resetting direction and/or induces a movement about a second small angle of rotation of the output shaft 3 or of the tool.

The angular velocity of the internal gear 7 during the oscillating movement is preferably different because of the different distances of the eccentric element 88 from the axis of rotation 19A: The eccentric gear 5A is preferably designed so that during the movement of the output shaft 3 or of the tool in the second direction mentioned above, in particular in the direction opposite the preferential direction or working direction or in a restoring direction, the angular velocity of the internal gear 7 is greater than that during the movement of the output shaft 3 or the tool in the first direction, in particular in the preferential direction or working direction.

The oscillating rotational movement of the output shaft 3 or a tool connected thereto resulting from the superimposed unidirectional rotational movement and oscillating movement is shown in FIG. 10: the output shaft 3 or the tool rotates alternately in a first direction of rotation 21 (also referred to above as the preferential direction or working direction in which material is removed) about a first angle of rotation and in a second direction of rotation 22 (opposite the preferential direction or working direction or also referred to above as the reverse direction, in which material that has been removed is conveyed away) which is essentially opposite the first direction of rotation 21, about a second angle of rotation, wherein the first and second angles of rotation are preferably of different amounts. According to the embodiment depicted here, for example, the angle of rotation of the first direction of rotation 21 is approximately 150° and the angle of rotation of the second direction of rotation 22 is approximately 30°. Clearly any other values for the angles of rotation are also possible as long as the angles of rotation have different amounts, for example, approximately 45° and 20°, 180° and 90°, 270° and 90°, 450° and 180°, etc. The direction of rotation shown in FIG. 10 is also just an example and it therefore equally possible to reverse the directions of rotation of the two directions of rotation 21, 22 shown in FIG. 10, i.e., then the direction of rotation 21 would be counterclockwise and the direction of rotation 22 would be clockwise.

The frequency of the oscillating movement of the output shaft 3 or of the tool is in the range of approximately 3-50 Hertz, in particular in the range of approximately 5-20 Hertz, in particular approximately 10 Hertz, for example.

Figure 5:
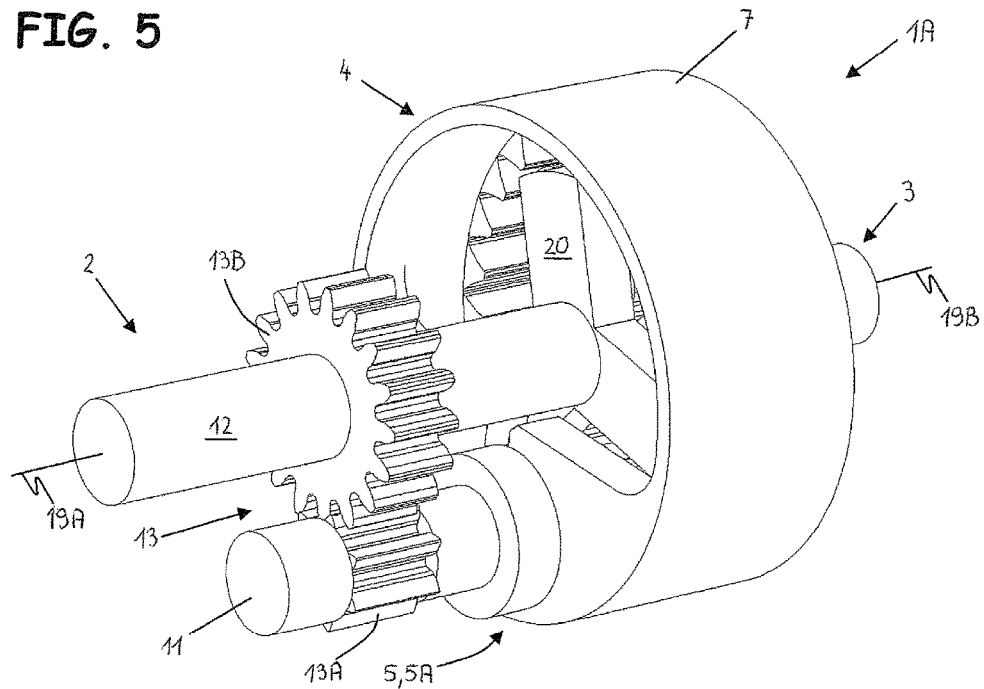
FIGS. 5-7 show a second embodiment of a drive device having a mechanical gear, which converts a unidirectional rotational movement into an oscillating rotational movement.
Figure 6:
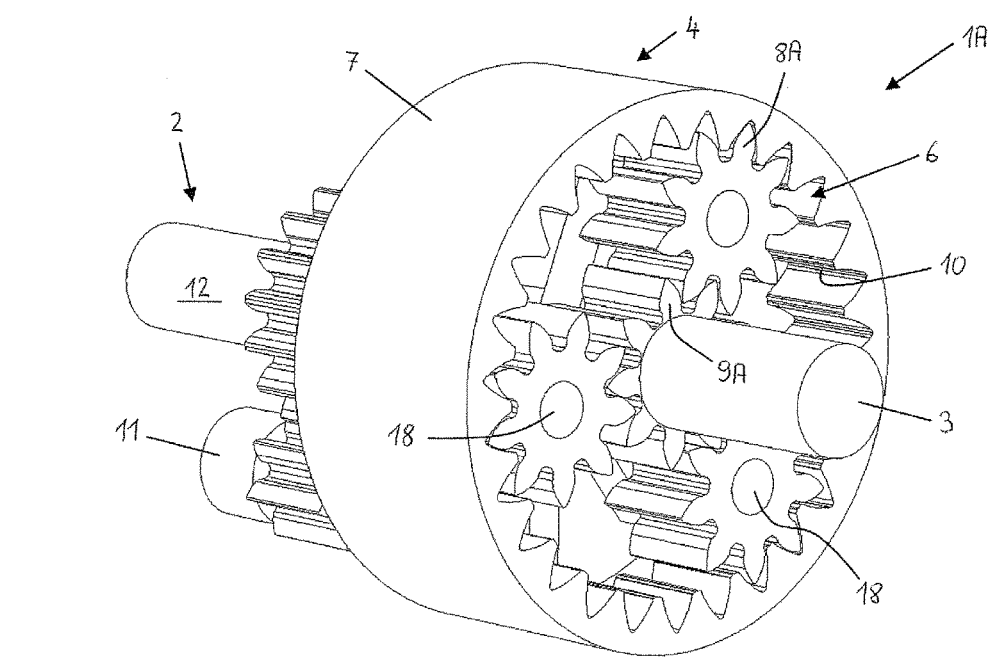
Figure 7:
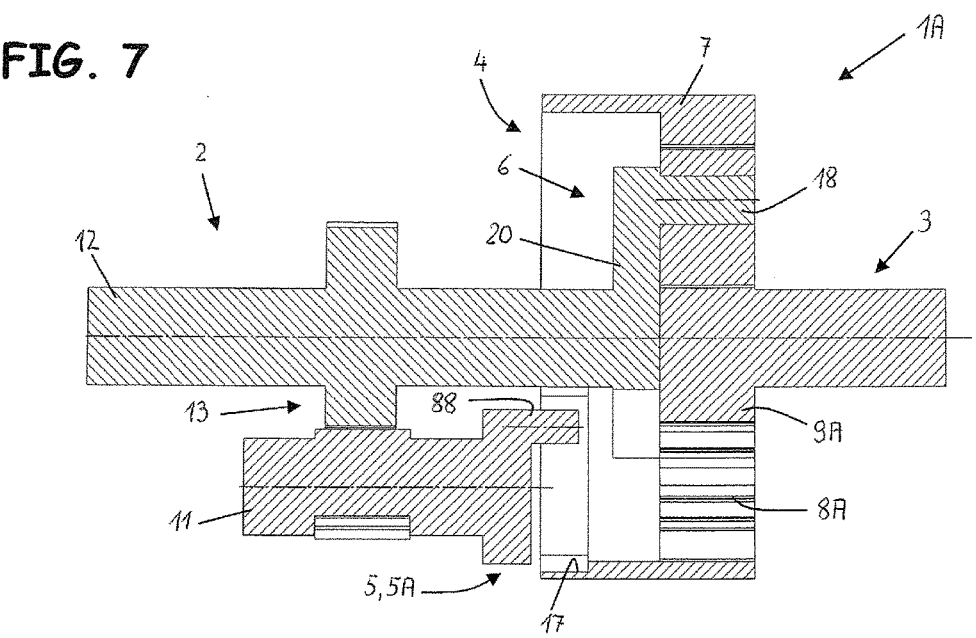
Figure 8A:
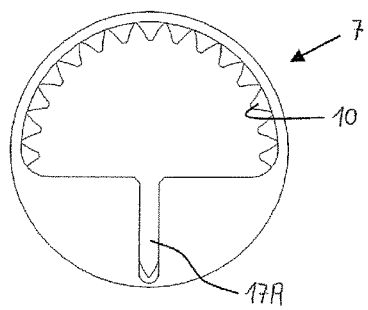
FIGS. 8A, 8B and 9A, 9B each show two different embodiments of internally geared internal gears which are part of the eccentric gear of the mechanical gear of the drive device in the front view and the rear view.
Figure 8B:
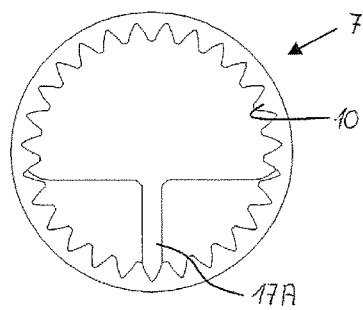
Figure 9A:
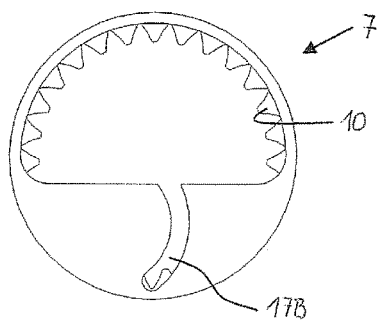
Figure 9B:
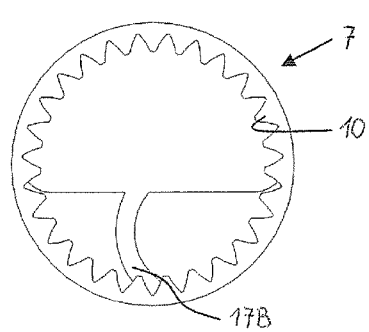

The functioning of the drive device 1A of FIGS. 5-7 is the same as the functioning of the drive device 1 described above. However, the design of the drive device 1A is different, inasmuch as the second drive shaft 12 is connected to the peripheral gearwheels 8A, preferable three such gearwheels, through the connecting elements 20 and the output shaft 3 is connected in a rotationally fixed manner to the central gearwheel 9A. The peripheral gearwheels 8A are in turn arranged to be rotatable in relation to the second drive shaft 12, in particular to be rotatable on the shaft sections 18 mounted on the connecting elements 20.

According to an embodiment a torque-limiting device for limiting the torque that can be transferred to the tool is provided on the drive device 1, 1A, in particular on the mechanical gear 4, for example, a friction clutch. The torque-limiting device may be arranged, for example, at the drive end, in particular on the drive shaft arrangement 2 or on at least one drive shaft 11, 12 or at the output end, in particular on the output shaft 3.

FIGS. 8A, 8B and 9A, 9B each show a front view and a rear view of embodiments of the internal gear 7 with different receptacles 17A, 17B, in particular groove-shaped or slot-shaped receptacles for the eccentric element 88. The receptacles 17, 17A, 17B may be designed straight, curved, essentially S-shaped, oblique, for example, or arranged centrally or eccentrically. Due to the variation in the shape and/or orientation of the receptacles 17, 17A, 17B of the eccentric gear 5A, the angle of rotation or the rotational speed of the internal gear 7, the output shaft 3 or a tool connected thereto can be varied, for example.

FIG. 11 shows a medical or dental treatment device 14, preferably a medical or dental handle element 14A, which is designed in particular for endodontic treatments, with a drive device 1, 1A, which is designed to induce an oscillating rotational movement of the tool. The mechanical gear 4 of the drive device 1, 1A is preferably surrounded by a sleeve 15 with a bearing 16, in particular a sliding bearing or a needle bearing, wherein the mechanical gear 4, preferably the eccentric gear 5A of the mechanical gear 4, especially preferably the internal gear 9 of the eccentric gear 5A of the mechanical gear 4 is rotatably supported on the sleeve 15, in particular on the bearing 16. The sleeve 15 preferably forms at least a part of the bearing 16, in particular of the sliding bearing. The sleeve 15 is formed, for example, by a gripping sleeve or an outer sleeve of the treatment device 14 or of the handle element 14A. Preferably, the gear 4, preferably the eccentric gear 5A, in particular the internal gear 7 of the eccentric gear 5A is supported rotatably by the bearing 16 in the treatment device 14 or the handle element 14A.

The treatment device 14 or the handle element 14A further comprises one or more of the following components: a tool-holding device 23 for releasably holding a tool that can be connected to the treatment device 14 or to the handle element 14A, wherein the tool-holding device 23 is connected to the output shaft 3 of the drive device 1, 1A so that the oscillating rotational movement can be transmitted to the tool-holding device 23; a motor drive, in particular an electric motor or a pneumatically operable motor; a coupling device 24 for connecting the treatment device 14 or the handle element 14A to a motor drive, in particular an electric motor or a pneumatically drivable motor and/or to a control and/or regulating device and/or to at least one media source, in particular a compressed air source or water source; a light source in particular with an optical semiconductor element that emits light for illuminating the preparation site and/or the tool; at least one media line for conveying a medium in the direction of the tool-holding device 23 and/or to the preparation site; a memory element, preferably re-writable, for storing identification data of the treatment device 14 or of the handle element 14A and/or operating data of the treatment device 14 or of the handle element 14A and/or default values; a temperature-measuring device, in particular in the area of the tool-holding device 23; a display device for display of operating data of the treatment device 14 or of the handle element 14A and/or of warnings.

Figure 14:
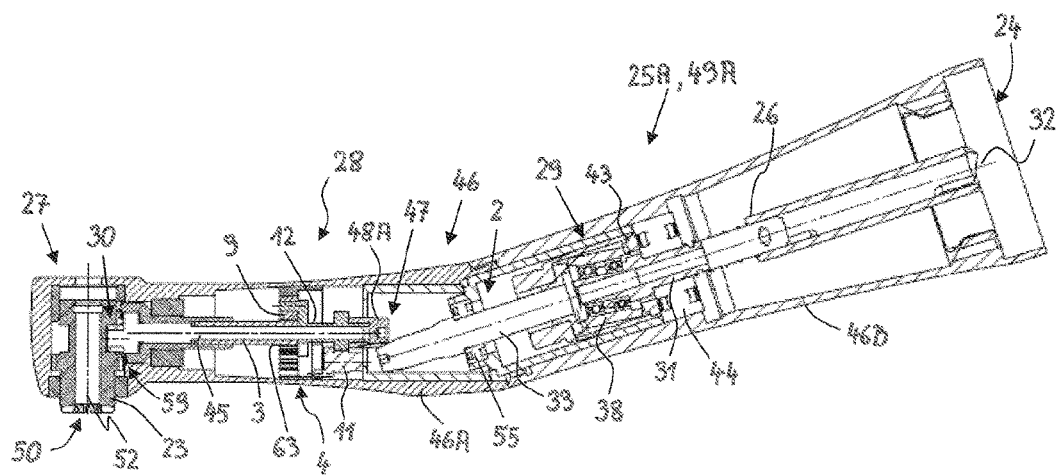
FIG. 14 shows a medical or dental treatment device with a gear arrangement having a gear for changing, in particular reducing, the rotational speed, an eccentric gear and a gear, which is designed to convert the unidirectional rotational movement transmitted by the drive shaft into an oscillating rotational movement, so that the tool-holding device of the treatment device can be induced to a, preferably simultaneous, lifting and oscillating rotational movement with an altered rotational speed.

FIGS. 12 and 14 show two treatment devices 25, 25A, in particular in the form of a handle element or handpiece or contra-angle handpiece 49, 49A. The features, which are the same with the two treatment devices 25, 25A, are described below. The treatment devices 25, 25A comprise: a head part 27 with a tool-holding device 23 accommodated therein and a handle part 46. The tool-holding device 23 is accommodated movably in the head part 27 and in particular it can be set to a, preferably simultaneous, rotational and lifting movement. The tool-holding device 23 is preferably designed to hold a tool releasably. According to FIGS. 12 and 14, the tool protrudes laterally through a tool receptacle opening 50 out of the head part 27 of the angle piece 49, 49A. The handle part 46 comprises a section 46A near the head and a rear section 46B arranged at an angle or curve to the former.

A drive shaft arrangement 2 extends from a coupling or connecting device 24 for connection of the treatment device 25, 25A or the handle element 49, 49A to a motor drive, in particular an electric motor or a pneumatically drivable motor and/or to a control and/or regulating device and/or to at least one media source, in particular a compressed air source or water source through the treatment device 25, 25A. The drive shaft arrangement 2 comprises one or more drive shafts 11, 12, 26, 31 which are designed for transmitting a unidirectional rotational movement. The unidirectional rotational movement is preferably made available by a motor drive which is detachably connectable to the coupling or connecting device 24 and the movement is transmitted to the drive shaft arrangement 2 through the coupling or connecting device 24. The at least one drive shaft 11, 12, 26, 31 is rotatably mounted in bearing elements 44, 55, preferably in roller bearings or ball bearings.

The two treatment devices 25, 25A additionally have a gear arrangement 28 comprising a plurality of mechanical gears to induce a, preferably simultaneous, rotational and lifting movement of the tool-holding device 23.

The gear arrangement 28 of the treatment device 25 is described in the following section (see FIG. 12): the gear arrangement 28 of the treatment device 25 comprises at least one gear 29 for changing, in particular reducing, the rotational speed of the unidirectional rotational movement (made available by the motor drive and transmitted by at least one drive shaft 26, 31) and an eccentric gear 30. The tool-holding device 23 can thus be induced to a rotational and lifting movement, which is preferably simultaneous and in which the rotational movement is formed by an essentially continuous rotation in one direction of rotation about an axis of rotation 52. Another mechanical gear 47 for transmitting and/or changing the rotational speed of the unidirectional rotational movement is preferably provided between the drive shaft 26 and an input shaft 31 of the gear 29 arranged at an angle to the former and/or a shaft 45 driving the eccentric gear 30, this mechanical gear 47 being designed, for example, as a 1:1 gear or as a step-down gear. The gear 47 comprises two gearwheels, wherein in particular one gearwheel 48 is arranged directly on the eccentric shaft 45 and/or on a shaft 31 driving the gear 29, so that the eccentric shaft 45 and the shaft 31 together can be driven by the gear 47.

Figure 13:
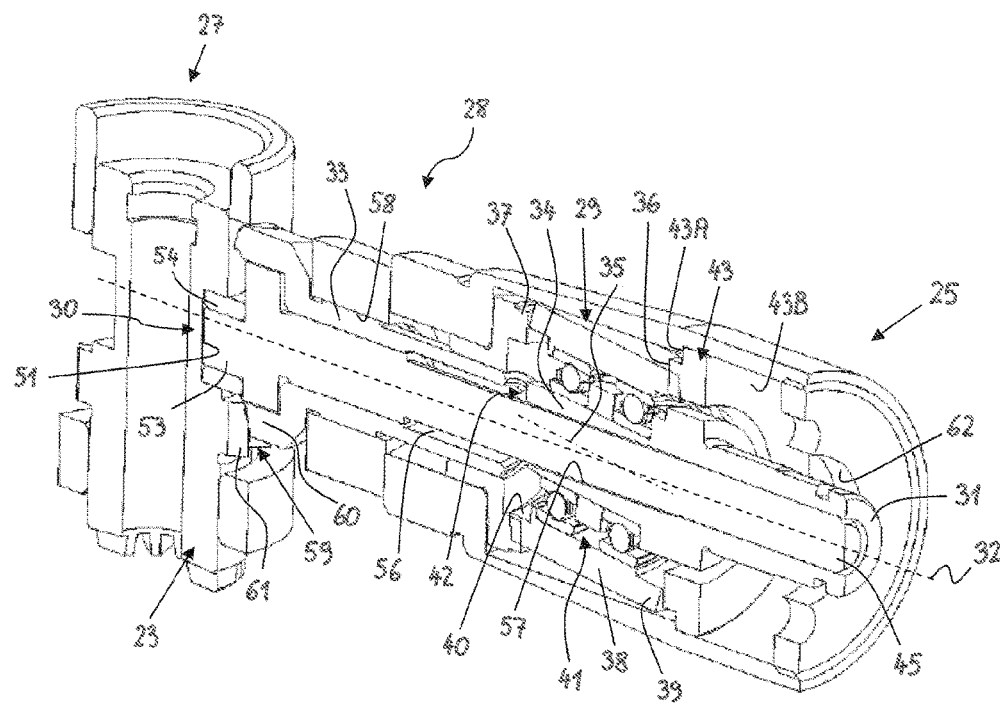
FIG. 13 shows the gear arrangement of FIG. 12 in an enlarged diagram.

The gears 29, 30 of the gear arrangement 28 of the treatment device 25 are illustrated in enlargement in FIG. 13. The gear 29 for changing, in particular reducing, the rotational speed of the unidirectional rotational movement comprises: an input shaft 31 with an axis of rotation 32, an output shaft 33 connected to the tool-holding device 23, an extension 34 connected to the input shaft 31 and having a central axis 35, wherein the central axis 35 is arranged at an angle to the axis of rotation 32 of the input shaft 31, a first row of teeth 36 arranged in a rotationally fixed position and having a plurality of teeth, a second row of teeth 37 arranged rotatably and connected to the output shaft 33 and having a plurality of teeth, a sleeve 38 arranged rotatably on the extension 34 connected to the input shaft 31, this sleeve having a third row of teeth 39 on its first end and a fourth row of teeth 40 on its second end, wherein the sleeve 38 is arranged between the first row of teeth 36 and the second row of teeth 37 so that at least one tooth of the third row of teeth 39 meshes with at least one tooth of the first row of teeth 36, and at least one tooth of the fourth row of teeth 40 meshes with at least one tooth of the second row of teeth 37. At least one bearing device 41 is provided on the extension 34 connected to the input shaft 31, for example, at least one roller bearing or ball bearing so that the sleeve 38 arranged on the extension 34 is rotatable in relation to the extension 34. One end of the extension 34 is designed as a free end 42 which extends freely and unsupported beyond the bearing device 41 in the direction of the tool-holding device 23. In addition a plate-shaped carrier 43 is provided with a first surface area 43A and a second surface area 43B arranged essentially parallel to the first surface area 43A. The first row of teeth 36, arranged in a rotationally fixed manner, is provided on the first surface area 43A so that its teeth point in the direction of the second row of teeth 37, wherein preferably the second surface area 43B is designed as a bearing seat for the bearing element 44 supporting the input shaft 31. The plate-shaped carrier 43 comprises a borehole 62, preferably centrally, through which the input shaft 31, for example, or a shaft 45 driving the eccentric gear 30 extends. All rows of teeth 36, 37, 39, 40 are designed in particular to be ring-shaped or circular.

Because of the inclination of the extension 34 of approximately 5°-15° with respect to the axis of rotation 32, the extension 34 and the sleeve 38 arranged thereon can be induced to a tumbling motion during operation, i.e., transmission of the unidirectional rotational movement. Only a few teeth but at least one tooth each, namely of the first and third rows of teeth 36, 39 as well as of the second and fourth rows of teeth 37, 40 mesh with one another during rotation of the sleeve 38 to form engagement sections. These engagement sections move or run along the rows of teeth 36, 37, 39, 40 during rotation of the sleeve 38. The engagement sections of the meshing rows of teeth 36, 39 and 37, 40 lie obliquely opposite the other because of the inclined arrangement of the sleeve 38: For example, if the engagement section of the rows of teeth 37, 40 is situated at the lower left, then the engagement section of the rows of teeth 36, 39 is at the upper right (see FIG. 13).

The number of teeth in the rows of teeth 36, 37, 39, 40 is, for example, approximately 10-30, wherein the desired step-down or step-up ratio is adjustable as a function of the actual number. The ratio of the rotational speed R1 of the input shaft 31 and the rotational speed R2 of the output shaft 33 is defined by the following relationship: R2/R1=1−(A*B)/(C*D), where A=number of teeth of the first row of teeth 36, B=number of teeth of the fourth row of teeth 40, C=number of teeth of the second row of teeth 37, D=number of teeth of the third row of teeth 39.

A geared connection 59 is provided between the output shaft 33 and the tool-holding device 23, to transmit the rotational movement of the output shaft 33 to the tool-holding device 23. The geared connection 59 comprise a gearwheel 60 on the output shaft 33 and a gearwheel 61 on the tool-holding device 23, in particular on the bushing or sleeve of the tool-holding device 23.

The eccentric gear 30 comprises, for example, an eccentric pin 53 preferably mounted in a bearing bushing 54, and a receptacle or a setback 51 for the eccentric pin 53, preferably on the tool-holding device 23. A shaft 45 can be set in rotation by means of the drive shaft 26 to drive the eccentric gear 30. The eccentric gear 30 induces a reciprocating or lifting movement of the tool-holding device 23 along the axis 52. Preferably at least a part of the eccentric gear 30, in particular eccentric pin 53 is provided directly on the shaft 45. The shaft 45 preferably passes through the gear 29 for changing the rotational speed of the unidirectional rotational movement. In particular the output shaft 33 including the gearwheel 60, the extension 34 and the input shaft 31 are designed as hollow shafts and have corresponding boreholes 56, 57 in which the shaft 45 is accommodated. The input shaft 31 and the eccentric shaft 45 are preferably connected to one another in a rotationally fixed manner, so that they can be driven together, for example, by a common drive shaft 26, a common gear 47 or a common motor drive. The output shaft 33 and the eccentric shaft 45 are preferably designed to be rotatable in relation to one another, wherein in particular a bearing 58, for example, a sliding bearing is provided on the inside of the output shaft 33 and the outside of the eccentric shaft 45.

The gear arrangement of the treatment device 25A shown in FIG. 14 comprises an eccentric gear 30, a gear 4, which is designed to convert the unidirectional rotational movement transmitted in particular by the drive shaft arrangement 2, 26 into an oscillating rotational movement and a gear 29 for changing, in particular reducing, the rotational speed of the unidirectional rotational movement. The eccentric gear 30 corresponds in its design and function to the eccentric gear 30 of FIGS. 12, 13. Therefore, to avoid repetition, the eccentric gear 30 will not be described again here.

The gear 4 for converting a unidirectional rotational movement into an oscillating rotational movement corresponds in its design and function largely to the gear of FIGS. 1-7, wherein the oscillating rotational movement comprises rotation of the tool alternately about a first angle of rotation in a first direction of rotation 21 and about a second angle of rotation 22 in a second direction of rotation 22, which is essentially opposite the first direction of rotation 21, wherein the first and the second angles of rotation 21, 22 are preferably of different amounts; therefore, only the differences are described in the following discussion: FIG. 14 shows that the gear 4 is arranged in the section 46A of the handle part 46 near the head. Accordingly the eccentric shaft 45 extends through the gear 4 and through the output shaft 3 which is designed as a hollow shaft. The gear 4, in particular the central gearwheel 9, 9A of the gear 4, thus comprises a borehole 63 for the eccentric shaft 45.

A mechanical gear 47 for transmitting and/or changing the rotational speed of the unidirectional rotational movement which is designed, for example, as a 1:1 gear or as a step-down gear, connects the gear 4 and the eccentric gear 30 to the drive shaft 26. The gear 47 comprises two gearwheels, wherein one gearwheel 48A in particular is arranged directly on the eccentric shaft 45 and/or on a shaft 11, 12 driving the gear 4, so that the eccentric shaft 45 and the shaft 11, 12 can be driven jointly by the gear 47. The eccentric shaft 45 and the shaft 11, 12 are preferably joined together in a rotationally fixed manner.

The gear 29 for changing, in particular reducing, the rotational speed of the unidirectional rotational movement also largely corresponds in its design and function to the gear of FIGS. 12, 13, so that only the differences are described in the following discussion: it can be seen from FIG. 14 that the gear 29 is arranged in the rear section 46B of the handle part 46. Since the eccentric shaft 45 is arranged in the section 46A of the handle part 46 near the head, the output shaft 33, the extension 34 or the input shaft 31 accordingly need not be designed as a hollow shaft, but instead at least one of these components may also be manufactured as a solid shaft. At least a part of the gear 47 is provided on the end of the output shaft 33 near the head, so that a unidirectional rotational movement having a reduced rotational speed can be transmitted to the gear 4, 30.

The treatment device 25A or the handle element 49A are thus designed on the basis of the gear arrangement 28 with the three mechanical gears 4, 29, 30 which convert the unidirectional rotational movement received or transmitted by the drive shaft 26 so, that the tool-holding device 23 can be induced to a, preferably simultaneous, lifting and oscillating rotational movement having a reduced rotational speed with respect to the rotational speed of the unidirectional rotational movement that is transmitted by the drive shaft 26.

The invention is not limited to the embodiments described here, but instead comprises all embodiments that use or include the basic logical function principle of the invention. It is thus also possible according to an alternative embodiment for the output shaft 3 to be connected directly and/or fixedly to the first element 5 for converting the unidirectional rotational movement transmitted by the drive shaft arrangement 2 into an oscillating movement, in particular an oscillating pendulum movement or pivoting movement, in particular to be connected to the eccentric gear 5A, preferably to the internal gear 7. In addition, according to this embodiment, a part of the first element 5, in particular of the eccentric gear 5A, for example, the eccentric element 88 or the receptacle 17 is/are provided on a carrier of the at least one peripheral gearwheel 8, for example, on the connecting element 20. The receptacle 17 is preferably arranged on the carrier of the at least one peripheral gearwheel 8 and the eccentric element 88, in particular in the form of a pin on the first shaft 11.

In addition, all the features of all the embodiments described and depicted here can be combined with one another. In particular the different mechanical gears 4, 29, 30 47 and their embodiments, which have been described here, may be combined with one another in any desired way or positioned in different locations on the treatment devices 14, 25, 25A.

We claim:

1. A drive device for a medical or dental tool, comprising:
   a drive shaft arrangement designed to transmit a unidirectional rotational movement;
   an output shaft designed to induce an oscillating rotational movement of the tool, wherein the oscillating rotational movement comprises an alternating rotation of the tool about a first angle of rotation in a first direction of rotation and about a second angle of rotation in a second direction of rotation, wherein the second direction of rotation is substantially opposite the first direction of rotation, and wherein the first angle of rotation and the second angle of rotation differ in magnitude from each other; and
   a mechanical gear drive assembly driveable by the drive shaft arrangement and configured to convert the unidirectional rotational movement transmitted by the drive shaft arrangement into the oscillating rotational movement and to transmit the oscillating rotational movement to the output shaft,
   wherein the mechanical gear drive assembly comprises a first element for converting the unidirectional rotational movement transmitted by the drive shaft arrangement into an oscillating pendulum movement, and a second element for transmitting the unidirectional rotational movement which is a part of the resulting output oscillating rotational movement.

2. The drive device of claim 1, wherein the first element for converting the unidirectional rotational movement transmitted by the drive shaft arrangement into the oscillating pendulum movement comprises an eccentric gear.

3. The drive device of claim 2, wherein the mechanical gear drive assembly comprises an internal gear and at least one part of the eccentric gear is provided on the internal gear.

4. The drive device of claim 3, wherein the internal gear is rotatable relative to the drive shaft arrangement.

5. The drive device of claim 1, wherein the second element for transmitting the unidirectional rotational movement comprises a plurality of gearwheels.

6. The drive device of claim 5, wherein at least one of the gearwheels of the plurality of gearwheels is rotatably coupled to the output shaft.

7. The drive device of claim 5, wherein the plurality of gearwheels comprises a first gearwheel which is centrally arranged and connected non-rotatably to the drive shaft arrangement or to the output shaft, and a second gearwheel which is peripheral relative to the first gearwheel and rotatably connected to the drive shaft arrangement or to the output shaft to rotate around the first gearwheel.

8. A drive device for a medical or dental tool, comprising:
   at least one drive shaft designed to transmit a unidirectional rotational movement;
   at least one output shaft designed to induce an oscillating rotational movement of the tool, wherein the oscillating rotational movement comprises an alternating rotation of the tool about a first angle of rotation in a first direction of rotation and about a second angle of rotation in a second direction of rotation, wherein the second direction of rotation is substantially opposite the first direction of rotation, and wherein the first angle of rotation and the second angle of rotation differ in magnitude from each other; and
   a mechanical gear drive assembly driveable by the at least one drive shaft and configured to convert the unidirectional rotational movement transmitted by the at least one drive shaft into the oscillating rotational movement and to transmit the oscillating rotational movement to the at least one output shaft, wherein the mechanical gear drive assembly comprises
   a pin and a receptacle for said pin to continuously and movably hold the pin within said receptacle; and
   a plurality of gearwheels, wherein the pin, the receptacle for said pin and the plurality of gearwheels are operatively interconnected such that the unidirectional rotational movement transmitted by the at least one drive shaft is converted into the oscillating rotational movement.

9. A medical or dental treatment device having the drive device of claim 8.

10. The drive device of claim 8, wherein the pin is arranged eccentrically in relation to an axis of rotation of the at least one drive shaft.

11. The drive device of claim 8, wherein the pin or the receptacle for said pin is coupled to the at least one drive shaft in order to be set into the unidirectional rotational movement transmitted by the at least one drive shaft.

12. The drive device of claim 8, wherein the plurality of gearwheels comprises an internally geared wheel.

13. The drive device of claim 8, wherein the plurality of gearwheels comprises at least one central gearwheel and at least one peripheral gearwheel which mesh with one another and which are moveably arranged relative to one another.

14. The drive device of claim 8, wherein the plurality of gearwheels comprises at least one gearwheel which is connected in a rotationally fixed manner to the at least one drive shaft or to the at least one output shaft.

15. The drive device of claim 8, wherein the pin or the receptacle for said pin is coupled to the at least one output shaft via at least one gearwheel of the plurality of gearwheels.

16. A drive device for a medical or dental tool, comprising:
- at least one drive shaft designed to transmit a unidirectional rotational movement;
- at least one output shaft designed to induce an oscillating rotational movement of the tool, wherein the oscillating rotational movement comprises an alternating rotation of the tool about a first angle of rotation in a first direction of rotation and about a second angle of rotation in a second direction of rotation, wherein the second direction of rotation is substantially opposite the first direction of rotation, and wherein the first angle of rotation and the second angle of rotation differ in magnitude from each other; and
- a mechanical gear drive assembly driveable by the at least one drive shaft and configured to convert the unidirectional rotational movement transmitted by the at least one drive shaft into the oscillating rotational movement and to transmit the oscillating rotational movement to the at least one output shaft, wherein the mechanical gear drive assembly comprises
- a pin and a receptacle for said pin to continuously and movably hold the pin within said receptacle; and
- a plurality of gearwheels, wherein the pin, the receptacle for said pin and the plurality of gearwheels are operatively interconnected such that an oscillating, pivoting movement generated by the pin and the receptacle for said pin is transmitted to at least one gearwheel of the plurality of gearwheels in order to obtain the oscillating rotational movement and to the at least one output shaft.

17. The drive device of claim 16, wherein the at least one gearwheel to which the oscillating, pivoting movement is transmitted comprises one of: an internally geared wheel; a gearwheel which is rotatably coupled to the at least one drive shaft or to the at least one output shaft.

18. The drive device of claim 16, wherein at least one gearwheel of the plurality of gearwheels is coupled to the at least one drive shaft such that the unidirectional rotational movement is transmitted from the at least one drive shaft to said at least one gearwheel and wherein the pin and the receptacle for said pin are operatively interconnected to said at least one gearwheel such that oscillating, pivoting movement generated by the pin and the receptacle for said pin superimposes the unidirectional rotational movement in order to obtain the oscillating rotational movement.

19. The drive device of claim 16, wherein the pin is arranged eccentrically in relation to an axis of rotation of the at least one drive shaft.

20. The drive device of claim 16, wherein the plurality of gearwheels comprises at least one central gearwheel and at least one peripheral gearwheel which mesh with one another and which are moveably arranged relative to one another.

* * * * *